(12) United States Patent
Kase et al.

(10) Patent No.: US 7,709,667 B2
(45) Date of Patent: May 4, 2010

(54) PROCESS FOR PRODUCING FAT OR OIL

(75) Inventors: Minoru Kase, Kamisu (JP); Keiji Shibata, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 367 days.

(21) Appl. No.: 11/409,080

(22) Filed: Apr. 24, 2006

(65) Prior Publication Data

US 2006/0258872 A1    Nov. 16, 2006

(30) Foreign Application Priority Data

Apr. 28, 2005  (JP) .............................. 2005-133123

(51) Int. Cl.
*C11B 3/02* (2006.01)
*A23D 9/00* (2006.01)

(52) U.S. Cl. ...................... 554/174; 426/601

(58) Field of Classification Search ............. 554/174; 426/611, 612, 601; 435/134, 135
See application file for complete search history.

(56) References Cited

U.S. PATENT DOCUMENTS

| | | | | |
|---|---|---|---|---|
| 2,383,581 | A * | 8/1945 | Arrowsmith et al. | 554/168 |
| 3,102,129 | A * | 8/1963 | Birnbaum et al. | 554/157 |
| 4,985,358 | A * | 1/1991 | Sawamura et al. | 435/134 |
| 6,004,611 | A | 12/1999 | Gotoh et al. | |
| 6,261,812 | B1 * | 7/2001 | Yamada et al. | 435/134 |
| 6,956,058 | B2 * | 10/2005 | Hase et al. | 514/547 |

FOREIGN PATENT DOCUMENTS

| | | |
|---|---|---|
| EP | 0 307 154 B2 | 12/1996 |
| JP | 63-133992 | 6/1988 |
| JP | 64-71495 | 3/1989 |
| JP | 8-294394 | 11/1996 |
| JP | 10-176181 | 6/1998 |
| JP | 11-123097 | 5/1999 |
| WO | WO 03/029392 * | 4/2003 |
| WO | WO 03/029392 A1 | 4/2003 |

OTHER PUBLICATIONS

Gezondheidsraad (=Health Counsil of the Netherlands), "Diacylglycerol Oil", XP-002396735, URL:www.cbg-rneb.nllnlldocslnwvoedingldiacylglycerololie.pdf>, 2002, p. 69.*
Cvengros, Three-Stage Wiped-film Molecular Evaproator; Design and Application, 1995, chem. Eng. Technol., vol. 18, pp. 49-58.*
Watanabe, T. et al., Diacylglycerol produciton in a packed bed bioreactor, 2004, Process Biochemistry, vol. 40, issue 2, pp. 637-643.*
Gezondheidsraad (=Health Counsil of the Netherlands), "Diacytglycerol Oil", XP-002396735, URL:www.cbg-meb.nl/nl/docs/nwvoeding/diacylglycerololie.pdf>, 2002, p. 69.
Takaaki Watanabe, et al.. "Diacylglycerol production in a packed bed bioreactor", Process Biochemistry, vol. 40, XP-004618217, Feb. 2005, pp. 637-643.

* cited by examiner

*Primary Examiner*—Porfirio Nazario-Gonzalez
*Assistant Examiner*—Yate' K Cutliff
(74) *Attorney, Agent, or Firm*—Oblon, Spivak, McClelland, Maier & Neustadt, L.L.P.

(57) ABSTRACT

A method for producing a diacylglycerol-rich fat or oil is provided. This method includes the steps of reacting an acyl group donor with an acyl group receptor, and separating unreacted material and byproducts by distillation for use as a part of the starting material in the subsequent cycle of production. The distillation is conducted such that the content of monoacylglycerol in the fat or oil after the distillation is 0.5 to 15% by weight.

9 Claims, No Drawings

PROCESS FOR PRODUCING FAT OR OIL

FIELD OF THE INVENTION

This invention relates to a process for producing a diacylglycerol-rich fat or oil containing diacylglycerol at a high content.

BACKGROUND OF THE INVENTION

A fat or oil containing diacylglycerol at a high concentration is known to have physiological benefits, such as a very low degree of accumulation in the human body (JP-A-10-176181), and therefore is widely used as an edible oil. It has already been known that diacylglycerol is produced by chemical or enzymatic esterification using a fatty acid and glycerine as the starting materials (JP-A-1-71495) or by chemical or enzymatic glycerolysis using a fat or oil and glycerine as the starting materials (WO 03/29392 and JP-A-63-133992).

Some of the diacylglycerol-rich fats or oils produced by such methods, however, contain impurities, such as fatty acid, monoacylglycerol and odor components. For the diacylglycerol-rich fat or oil to be used as an edible oil, it is desirable to have a better flavor by reducing such impurities.

Among the methods of producing a diacylglycerol-rich fat or oil, there is a technique by which the fat or oil after the completion of the reaction is further purified and the monoacylglycerol recovered is added to the starting material of the subsequent cycle of the reaction (JP-A-8-294394). This technique is aimed to improve the speed of the esterification by increasing solubility of the glycerine in the fatty acid phase by adding the monoacylglycerol which has been collected upon removal of the impurities unsuitable for an edible oil by distillation under high vacuum conditions to the reaction system of the subsequent reaction cycle. Besides, there is another method by which the glycerine and monoacylglycerol remaining in the reaction system after completion of chemical glycerolysis using a fat or oil and glycerine as the starting materials are recovered by steam distillation or molecular distillation for use in the subsequent cycle of the reaction (WO 03/29392). This method is economically advantageous in that this method does not require the step of decomposing the fat or oil for use of the decomposition products in the subsequent esterification. Further, there is a technique requiring that an esterification reaction be performed after the partial hydrolysis of fat or oil without distillation, so that a trace of substances, such as phytosterol, could still be contained in the diacylglycerol product (JP-A-11-123097). While this technique has such an advantage, it should be noted that the concentration of the diacylglycerol obtained thereby is too low, and no consideration is made for re-use of the unreacted substances or the by-products.

SUMMARY OF THE INVENTION

This invention provides a process for producing a diacylglycerol-rich fat or oil including the steps of reacting an acyl group donor with an acyl group receptor; and separating the unreacted material and the byproducts by distillation for use as a part of the starting material in the subsequent cycle of production; in which the distillation is conducted such that the content of monoacylglycerol in the fat or oil after the distillation is 0.5 to 15% by weight.

DETAILED DESCRIPTION OF THE INVENTION

In recent years, there has been a growing social demand for solving environmental problems, and at the same time there is a strong need to establish a production technique, which can satisfy both the demand for obtaining high quality products and the need for lessened environmental burden. In order to lessen the environmental burden, it is effective to minimize the amount of waste products emerging from a production process. Hence, in a process for producing a diacylglycerol-rich fat or oil, it is desirable to develop a new technique wherein reusable substances among waste products are collected selectively and then reused for subsequent productions.

When a diacylglycerol-rich fat or oil is produced by the conventional method as described above, the resulting fat or oil should be subjected to a further removal of the fatty acids, monoacylglycerol, odor components, and the like which are unsuitable in terms of components of an edible oil. Removal of such components, however, leads to the removal of biologically useful components such as tocopherol and phytosterol that are included in the fat or oil used as the starting material. As described above, an alternative technique is proposed that is characterized by the removal of the glycerine from the diacylglycerol-rich fat or oil and the monoacylglycerol remaining in the reaction system by conducting steam distillation or molecular distillation to use the removed fraction in the subsequent cycle of the production. However, this technique still has some problems in that the biologically advantageous components included in the fat or oil are removed simultaneously as a result of the molecular distillation carried out under high vacuum conditions, and the biologically unsuitable trans unsaturated fatty acid are generated because of its severe heat history. Furthermore, the aforementioned technique, which consists of a partial hydrolysis of fat or oil and then an esterification reaction without distillation, is not only environmentally detrimental but also economically disadvantageous, because of its ability for generating a large volume of waste products. Besides, there is a problem that even though the unreacted ingredients and the by-products can be reused for subsequent productions, these are partially disassembled at an extremely low level and therefore lower the concentration of the diacylglycerol contained in the products, so that a majority of the unreacted ingredients and by-products remain unused, and the fraction recovered as a result of such a process becomes proportionately large. Hence, this technique cannot be said to be effective.

Diacylglycerol which is less hydrophobic than triacylglycerol has high affinity for the fatty acid and the monoacylglycerol, and therefore makes it difficult to remove the fatty acid and the monoacylglycerol. Accordingly, strict conditions are required for the removal of the impurities to attain an improved purity of the diacylglycerol and purity as an edible oil. However, such strict conditions invites unfavorable results such as the formation of the trans unsaturated fatty acid due to the severe heat history, a decrease in the purity due to disproportionation, and a loss of biologically useful components included in the fat or oil used as the starting material.

In view of the situation as described above, the present invention provides a highly efficient and environmentally less detrimental process for producing a diacylglycerol-rich fat or oil which has an improved diacylglycerol purity as well as an improved degree of purification as an edible oil while retaining the biologically advantageous components of the fat or oil used in the production of the fat or oil product.

The inventors made an extensive investigation on the process for producing a diacylglycerol-rich fat or oil, and found that production of the trans-unsaturated fatty acids can be suppressed while maintaining the phytosterols and other advantageous components of the fat or oil used in the production in the fat or oil product, and also increasing the diacylglycerol content of the distillation after the reaction is conducted under a particular set of conditions and the fraction collected by such distillation is recycled in the subsequent cycle of the production.

Examples of an acyl group donor used as a starting material in the embodiments of the method of the present invention include triacylglycerols such as vegetable oils, for example, rapeseed oil, soybean oil, sunflower oil, palm oil, and linseed oil and animal oils such as beef tallow and fish oil; a fatty acid produced by hydrolysis of such fat or oil; and lower alcohol esters of such fatty acids. Among these, vegetable oils having a high content of unsaturated fatty acid and fatty acids produced by the hydrolysis of such vegetable oil are preferable, with more preferably rapeseed oil, soybean oil, and fatty acids produced by the hydrolysis of such oil in view of a favorable physiological function and an outer appearance of the resulting product with no turbidity. Such acyl group donor may be used either alone or in combination of two or more. The content of the unsaturated fatty acid in the total acyl group donor is preferably 60% by weight (hereinafter referred to as "%" for simplicity) or higher, more preferably 70% or higher, and even more preferably 80% or higher. The content of the monoenoic acid in the unsaturated fatty acid is preferably 10 to 80%, and more preferably 15 to 70%; the content of the dienoic acid in the unsaturated fatty acid is preferably 10 to 80%, and more preferably 15 to 60%; and the content of the trienoic acid in the unsaturated fatty acid is preferably 0.2 to 70%, and more preferably 0.5 to 60%. When two or more acyl group donors are used, the content of such unsaturated fatty acid is the total of the acyl group donors used. An exemplary acyl group receptor is glycerol.

Exemplary methods for producing a diacylglycerol-rich fat or oil of the embodiments of the present invention include a method using chemical or enzymatic esterification wherein the starting material contains a fatty acid produced by hydrolysis of the fat or oil as described above, or an ester of such fatty acid with a lower alcohol (an acyl group donor) and glycerine (an acyl group receptor); and a method using chemical or enzymatic glycerolysis wherein the starting material contains the fat or oil as described above (acyl group donor) and glycerine (an acyl group receptor). Among these, the preferred is a method using esterification of a fatty acid with glycerine in view of the capability of adjusting the fatty acid composition of the product and improving the diacylglycerol purity. Still more preferred is the enzymatic esterification in view of suppressing formation of the trans unsaturated fatty acids, its capability of regulating the fatty acid composition of the product, and improving the diacylglycerol purity. When the product to be produced has a fatty acid composition similar to the fat or oil used in the starting material, preferred is a method using glycerolysis of a fat or oil with glycerine in view of simplifying the production process. It should also be noted that a method using chemical glycerolysis is preferable to reduce the reaction time and improve the productivity, and a method using enzymatic glycerolysis is preferable to suppress the formation of the trans unsaturated fatty acids.

The fat or oil used in the embodiments of present invention may be prepared by pressing a fat or oil from the source plant or animal; removing solid contents other than the fat or oil component by centrifugation or other method; and degumming the fat or oil by adding water and an optional acid, stirring, and separating the gummy contents by centrifugation or other method. Preferably, the fat or oil is further deacidified by adding an alkaline, stirring, and washing with water; and further decolorized by bringing the fat or oil in contact with an adsorbent such as active clay, and separating the adsorbent by filtration or other method. Although the treatments as described above are preferably carried out in the order as described above, these treatments may be carried out in other orders. The fat or oil may be further subjected to the step of wintering wherein the solid contents are separated at a low temperature for the removal of the wax content. Preferably, the fat or oil is further deodorized by bringing the fat or oil in contact with steam under reduced pressure. In order to suppress the formation of the trans unsaturated fatty acids, the fat or the oil is preferably deodorized with minimal heat history at a temperature controlled to the range of up to 30° C., and in particular, to the range of up to 270° C. in a reaction time within the range of up to 10 hours, and in particular, up to 5 hours.

The content of the trans unsaturated fatty acid in the total fat or oil used as the starting material in the embodiment of the present invention is preferably up to 1.5%, more preferably up to 1%, and even more preferably up to 0.5% in view of reducing the trans unsaturated fatty acid content in the final product. When two or more fats or oils are used, the trans unsaturated fatty acid content is the total content of such fats or oils. The trans unsaturated fatty acid content in the fat or oil used for the starting material may be measured by the Official Method of the American Oil Chemists' Society, Ce 1f-96 (a GLC procedure).

When a diacylglycerol-rich fat or oil is produced by esterification of a fatty acid and glycerine in the embodiments of the present invention, the fat or oil used for the starting material is hydrolyzed before the esterification. The hydrolysis of the fat or oil used for the starting material may be accomplished by a high pressure decomposition or by an enzymatic decomposition, or a combination thereof. When the trans unsaturated fatty acid content is minimized, all of the fat or oil used for the starting material is preferably hydrolyzed by an enzymatic decomposition with minimal heat history. When hydrolysis is conducted by a high pressure decomposition, proportion of the fat or oil used for the starting material is preferably 30% or more in view of the color of the resulting fatty acid, or in view of improving the flavor and color of the glyceride. When hydrolysis is conducted by a high pressure decomposition, the proportion of the fat or oil used for the starting material is more preferably 35 to 95%, and more preferably 40 to 90% in view of reducing the trans unsaturated fatty acid and improving the flavor and color.

When the fat or oil used for the starting material already has a high content of the trans unsaturated fatty acids in the fatty acids constituting the fat or oil, the hydrolysis is preferably carried out by enzymatic decomposition in view of minimizing the further increase of the trans unsaturated fatty acid content in the resulting fatty acid, or the fat or oil. When the fat or oil used for the starting material has a low trans unsaturated fatty acid content, the hydrolysis is preferably conducted by a high pressure decomposition in view of the higher process efficiency and improving the flavor and color. When the hydrolysis is conducted by such high pressure method, the trans unsaturated fatty acid content in the fatty acids constituting the fat or oil used for the starting material is preferably up to 1%, more preferably up to 0.8%, and even more preferably up to 0.5%.

Since a fat or oil used for the starting material containing fatty acid constituents with a higher degree of unsaturation is more likely to produce trans isomer by heating, such fat or oil having a high content of fatty acids with a high degree of unsaturation is preferably hydrolyzed by an enzymatic decomposition. More specifically, oleic acid having a degree of unsaturation of 1 undergoes little trans isomer formation by the heating, while a fatty acid with the degree of unsaturation of 2 or higher undergoes more significant trans isomer formation. Accordingly, a fat or oil used for the starting material containing the constituent fatty acids having the degree of unsaturation of 2 or more at a content of at least 40%, more particularly at least 50%, and even more particularly at least 60% is preferably hydrolyzed by an enzymatic decomposition. Since the trans isomer formation becomes significant with the increase in the degree of unsaturation, a fat or oil used for the starting material containing 10% or more of the constituent fatty acids with the degree of unsaturation of 3 or more is preferably hydrolyzed by enzymatic decomposition.

The high pressure decomposition is preferably carried out by using high pressure hot water at a temperature of 220 to 270° C., and the fat or oil used for the starting material is preferably hydrolyzed in 2 to 6 hours. A low temperature is preferred in view of suppressing the formation of the trans unsaturated fatty acid, but a high temperature is preferred in view of shortening the reaction time and simplifying the equipment necessary for high-pressure reaction. The temperature of the high pressure hot water is more preferably 225 to 265° C., even more preferably 230 to 260° C., and even more preferably 235 to 255° C. The reaction time is preferably 2 to 5 hours, and more preferably 2 to 4 hours.

The enzyme used for the enzymatic decomposition in the hydrolysis of the fat or oil is preferably lipase which may be a commercially available lipase derived from an animal, a vegetable, or a microorganism.

The hydrolysis does not have to be accomplished to 100% decomposition degree, and an optimal decomposition degree may be selected. The term "decomposition degree" of the hydrolysis is the acid value of the decomposed oil/saponification value. The decomposition degree is preferably 67 to 98% in case of the high pressure decomposition, more preferably 80 to 95%, even more preferably 83 to 95%, and even more preferably 90 to 94%, for the ease of the hydrolysis process. In case of the enzymatic decomposition, meanwhile, the decomposition degree is preferably 50 to 98%, more preferably 67 to 96%, even more preferably 75 to 94%, even more preferably 80 to 92%, and even more preferably 85 to 90%, for the ease of the hydrolysis process. The decomposition degree within such range enables use of an adequately sized apparatus for the hydrolysis, reduced reaction time of the esterification, prevention of thermal deterioration of the quality, suppression of the increase of the trans unsaturated fatty acid, and improvement of the diacylglycerol purity of the final product. In addition, it is preferred to make the decomposition degree larger in view of the following benefits: the concentration of diacylglycerol contained in the product can be increased; the amount of the fraction returned by the distillation performed after reaction can be lowered; and the burden on reuse can be reduced.

The fatty acid produced by the hydrolysis may be used with no further purification, or after further adjustment of the fatty acid composition by purification by distillation, wintering, or the like.

Both chemical synthesis and enzymatic method may be used in the esterification of the fatty acid with the glycerine or the glycerolysis of the fat or oil with the glycerol. Among these, however, the preferred is the enzymatic method in view of preventing the increase in the content of the trans unsaturated fatty acid in the final fat or oil product.

The enzyme used in the esterification or the glycerolysis is preferably lipase, and in particular, when it is used for producing diacylglycerol which is used as a functional fat or oil, the lipase preferably used is the one belonging to Rizopus, Aspergillus, Mucor, Pseudomonas, Geotrichum, Penicillium, or Candida which is capable of producing the diacylglycerol at a high selectivity.

The enzyme used in the esterification or the glycerolysis is preferably an immobilized enzyme in view of economy.

When the esterification or the glycerolysis is conducted by an enzymatic method, the reaction temperature is preferably in the range of 0 to 100° C., more preferably 20 to 80° C., and even more preferably 30 to 80° C. in view of improving the reaction speed and suppressing the enzyme inactivation.

When the esterification or the glycerolysis is conducted by a chemical method, the reaction temperature is preferably in the range of 100 to 300° C., and more preferably 150 to 250° C. in view of increasing the reaction speed and suppressing the formation of the trans unsaturated fatty acid. Use of a catalyst such as an alkaline such as sodium hydroxide or calcium hydroxide, or an acid such as an organic acid or its salt is preferred in view of increasing the reaction speed and improving the color of the treated oil that has undergone the esterification or glycerolysis.

When the esterification is conducted by an enzymatic method, the reaction system is preferably dehydrated by reducing the reaction pressure in view of increasing the diacylglycerol content in the treated oil. When the esterification is conducted by a chemical method, the reaction system is preferably dehydrated by flowing inert gas in view of increasing the diacylglycerol content in the treated oil.

In the esterification or the glycerolysis, the starting material is preferably charged so that the ratio of the molar number of the fatty acid group to the molar number of the glycerine group is in the range of 0.2 to 10, more preferably 0.3 to 8, even more preferably 0.5 to 6, and even more preferably 0.5 to 4 in view of optimizing the composition of the treated oil. When the ratio is within such range, the amount of the fatty acid and the glycerine remaining in the treated oil as well as the amount of the monoacylglycerol and triacylglycerol produced will be reduced to allow for easier distillation, and the content of the diacylglycerol will be increased to thereby realize an improved production efficiency. This ratio of the molar number of the fatty acid group to the molar number of the glycerine group is hereinafter referred to as "FA/GLY". This FA/GLY is represented by the following equation:

FA/GLY=(molar number of the fatty acid+molar number of the lower alcohol ester of the fatty acid+molar number of the monoacylglycerol+molar number of the diacylglycerol×2+molar number of the triacylglycerol×3)/(molar number of the glycerine+molar number of the monoacylglycerol+molar number of the diacylglycerol+molar number of the triacylglycerol)

The FA/GLY may be adequately selected depending on the type of the reaction. For example, when the esterification or the glycerolysis is conducted by an enzymatic method, the FA/GLY is preferably in the range of 1 to 3, more preferably 1.5 to 2.5 in view of optimizing the composition of the treated oil. When the esterification or the glycerolysis is conducted by a chemical method, the FA/GLY is preferably in the range of 0.3 to 3, more preferably 0.4 to 2.2 in view of optimizing the composition of the treated oil.

In addition to the diacylglycerol, the treated oil which has undergone the esterification contains the unreacted fatty acid and glycerine as well as the byproduct triacylglycerol and monoacylglycerol.

In the case of the treated oil which has undergone glycerolysis, the oil contains the unreacted glycerine and the triacylglycerol and the byproduct monoacylglycerol in addition to the diacylglycerol.

The content of the monoacylglycerol in the treated oil after the esterification or the glycerolysis is preferably in the range of 2 to 60%, more preferably 3 to 50%, even more preferably 5 to 50%, and even more preferably 10 to 50% in view of increasing the diacylglycerol content in the product, ease of the subsequent distillation, and improving the reaction efficiency. The content of the diacylglycerol in the treated oil after the esterification or the glycerolysis is preferably in the range of 10 to 90%, more preferably 20 to 80%, even more preferably 30 to 70%, and even more preferably 30 to 60% in view of increasing the diacylglycerol content in the product, allowing for easier distillation, and improving the reaction efficiency.

In the present invention, the fatty acids, the glycerine, and the monoacylglycerol are recovered by distillation for reuse in the subsequent production cycles.

The content of the monoacylglycerol in the fat or oil after the distillation in the embodiments of the present invention should preferably be in the range of 0.5 to 15% in order to leave the phytosterol of the starting fat or the oil in the resulting fat or oil, and to increase the diacylglycerol content. The monoacylglycerol content is preferably 0.5 to 10%, more preferably in the range of 0.5 to 8%, even more preferably 1 to 8%, and even more preferably 1.3 to 8%. Although the weight of the fraction collected may differ by the composition of the treated oil, the weight of the collected fraction is preferably 0.5 to 1.5 folds, more preferably 0.6 to 1.4 fold, and even more preferably 0.6 to 1.2 folds of the weight of the components of the treated oil other than the diacylglycerol and the triacylglycerol in view of controlling the monoacylglycerol content in the range of 0.5 to 15%, improving the diacylglycerol yield, and avoiding the recycling of an excessive amount of distillated fraction. The content of monoacylglycerol contained in the distillated fat or oil is preferably 0.03 to 0.8, more preferably 0.05 to 0.6, and even more preferably 0.1 to 0.5 with respect to the monoacylglycerol content in the reacting oil, from the view point of leaving phytosterol derived from raw material fat or oil in the fat or oil and increasing the diacylglycerol content in the product.

Conditions of the distillation used in the embodiments of the present invention preferably include a pressure of 2 to 300 Pa, more preferably 3 to 200 Pa, and even more preferably 3 to 100 Pa in view of reducing the cost of installation and operation, improving distillation ability, adequate selection of the distillation temperature, and suppressing the increase of the trans unsaturated fatty acid by heat history. The temperature used is preferably 180 to 280° C., more preferably 190 to 260° C., and even more preferably 200 to 250° C. in view of suppressing the increase of the trans unsaturated fatty acid. The residence time is preferably 0.2 to 30 minutes, more preferably 0.2 to 20 minutes, and even more preferably 0.2 to 10 minutes also in view of suppressing the increase of the trans unsaturated fatty acid. The "residence time" is the average of the residence time during which the fat or the oil is at or over the distillation temperature.

With regard to the distillation conditions used in the embodiments of the present invention, the pressure and the temperature as described above are preferably further adjusted so that the monoacylglycerol content in the fat or oil after the distillation is in the range of 0.5 to 15%. Other conditions which may be used in adjusting the monoacylglycerol content include feed rate as well as liquid film thickness when a thin film evaporator is used. For example, when the content of the monoacylglycerol in the fat or oil after the distillation is less than 0.5% under the conventional distillation conditions, the adjustment may be accomplished by a means or a combination of two or more means selected from (1) increase in the pressure (decrease in the degree of vacuum), (2) decrease in the temperature, (3) increase of the feed rate, (4) increase of the liquid film thickness when a thin film evaporator is used, and the like. More specifically, when the content of the monoacylglycerol in the fat or oil after the distillation is in the range of 0.05 to 0.4% under conventional conditions, and the content of the monoacylglycerol in the fat or oil after the distillation is to be increased to the level of 0.5 to 15%, the pressure is preferably increased to 1.1 to 20 folds, and/or the temperature is reduced by 5 to 50° C., and/or the feed rate is increased to 1.1 to 10 folds of the conventional conditions respectively.

In the embodiments of the present invention, the treated oil may be pre-distilled at a low degree of vacuum and/or at a low temperature before the distillation process as described above in order to ensure stability of the distillation process. When the treated oil has a high content of the glycerine and the treated oil separates into two liquid phases, the glycerine phase is preferably separated by the liquid-liquid separation operation before the distillation process. The separated fraction may be recycled in the subsequent cycle of production as a part of the starting material.

The unreacted material and the byproducts are removed in conventional purification step under the conditions including a pressure of 1 to 500 Pa, a temperature of 200 to 300° C., and a residence time of 1 to 10 hours. Such conditions, however, are unfavorable, since the reactants are exposed to an excessively severe heat history, and the generation of trans unsaturated fatty acid will increase when the unreacted material is recovered and used in the subsequent cycle of the production.

A distillation method often used to avoid the fat or oil from being exposed to an excessively severe heat history is molecular distillation which is conducted under a high vacuum at a pressure of 0.01 to 1 Pa. In this case, the distillation can be conducted at a relatively low temperature of 150 to 200° C. However, necessity for the high vacuum results in the strict requirement for the vacuum installation and reduced distillation capacity, and also, in the removal of various biologically advantageous trace elements such as phytosterol that had been included in the fat or oil used as the starting material. Accordingly, this method is not preferable.

The conditions required to realize the monoacylglycerol content of 0.5 to 15% for the fat or oil after the distillation may be determined based on the vapor pressure curves of the components included. The "vapor pressure curve" is a curve showing vapor pressure of the substance at different temperatures. The conditions are preferably adjusted so that the temperature and the pressure of the distillation residue (the fat or oil after the distillation) at the completion of the distillation step (at the exit of the distillation step in the case of continuous distillation) fall between the vapor pressure curve of the monoacylglycerol and the vapor pressure curve of the diacylglycerol. When the distillation is operated at a particular pressure, the amount of heat applied is preferably controlled such that the temperature of the distillation residue (the fat or oil after the distillation) at the completion of the distillation step (at the exit of the distillation step in the case of continuous distillation) is higher than the evaporation temperature of the monoacylglycerol at that particular pressure and lower than the evaporation temperature of the diacylglycerol at that particular pressure. Alternatively, conditions used for the distillation may be determined by conducting distillation calculations using vapor pressure curves and liquid-vapor equilibrium estimation equations of the components involved.

Exemplary distillation apparatus which may be used in the present invention include a batchwise simple distillation apparatus, a batch rectifier, a continuous rectifier, a flash distillation apparatus, and a thin film distillation apparatus, and the preferred among these is a thin film distillation apparatus in view of realizing the conditions required for the distillation. A thin film distillation apparatus is a distillation apparatus wherein the material to be distilled is heated in the form of a thin film to thereby facilitate evaporation of the component to be fractionated. Examples of such thin film distillation apparatus include centrifugal thin film distillation apparatus, falling film distillation apparatus, and wiped film distillation apparatus which differ in the method used in forming the thin film. Among these, the preferred is wiped film distillation apparatus in view of preventing local overheating and avoiding thermal degradation of the fat or oil. In the case of a wiped film distillation apparatus, the material subject to distillation is allowed to run down on the inner surface of a heated cylindrical evaporator in the form of a thin liquid film while this thin film is wiped with a wiper, and the evaporator is externally heated for evaporation of the component to be fractionated. Of the wiped film distillation apparatus, the preferred is the one wherein the distilled fraction is condensed by a condenser located inside the distillation apparatus in view of reducing the cost of the vacuum system by reducing pumping resistance, and increasing the evaporation capacity. Exemplary wiped film distillation apparatus include "Short Path Distillation Unit" manufactured by UIC GmbH, "Wiprene" manufactured by Shinko Pantec Co., Ltd., and "Kontro" manufactured by Hitachi, Ltd.

In the present invention, the fraction collected in the distillation is used as a part of the starting material in the subsequent cycle of the reaction. The composition of the fraction collected may differ depending on the composition of the treated oil. However, the fraction collected may preferably contain about 5 to 80% of the monoacylglycerol, about 0.5 to 60% of the fatty acid, and about 0.5 to 30% of the glycerol. The amount of the starting material used may be determined depending on the composition of the fraction collected. The reaction conditions used in the subsequent cycles of the reaction are preferably the same as those used in the preceding cycle.

In the embodiments of the present invention, recycling of the fraction collected by the distillation as a part of the starting material in the subsequent production cycle is preferably repeated for two or more production cycles in view of suppressing the formation of the trans unsaturated fatty acid, efficiently obtaining a fat or oil containing the phytosterol and other useful components that had been included in the fat or oil as the starting material, and reducing the amount of waste products. The fraction returned to the subsequent production cycle as part of the starting material may be either all or a part of the fraction collected by the distillation. When a part of the fraction collected by the distillation is used as part of the starting materials in the subsequent production cycle, the part recycled is preferably 50% or more to less than 100%, more preferably 60% or more and less than 100%, and 70% or more to less than 100% of the fraction collected by the distillation. By using the returned fraction as part of the starting materials for the subsequent production cycle, it becomes possible not only to reduce the waste products significantly, but also minimize the environmental burden caused by the production process. As it turns out, the amount of the waste products is preferably reduced in the range of 1 to 100%, more preferably 5 to 90%, even more preferably 20 to 80%, compared with a case when there is no recycling of the fraction.

In addition, when the diacylglycerol-rich fat or oil produced in two or more cycles of the esterification between the fatty acid and the glycerine or the glycerolysis between the fat or oil and the glycerine are mixed to produce the fat or oil product, the product may preferably contain 50% or more, more preferably 60% or more, even more preferably 70% or more, and even more preferably 80 to 100% of the diacylglycerol-rich fat or oil produced by the method of the present invention in view of suppressing the formation of the trans unsaturated fatty acid and efficiently producing a fat or oil containing the phytosterol and other components that had been included in the fat or oil used as the starting material.

After the distillation as described above, the diacylglycerol-rich fat or oil is preferably subjected to distillation by a conventional method, such as decoloration, deodoration, and the like which are conducted for purification by removing or decomposing the remaining fatty acids, monoacylglycerol, coloring components, odor components, and the like. The diacylglycerol-rich fat or oil after the distillation or the purification as described above may be further subjected to a distillation wherein the diacylglycerol is obtained as the distillate leaving the triacylglycerol and the high-boiling components as the distillation residue to thereby produce a diacylglycerol-rich fat or oil having a still higher diacylglycerol content. The triacylglycerol and other components recovered as the distillation residue in this step are preferably reused as a part of the starting material with or without further purification in view of the efficient use of the reaction material.

The diacylglycerol-rich fat or oil produced by the method of the present invention may preferably contain the diacylglycerol at a content of 40% or higher, more preferably at 50% or higher, even more preferably at 60% or higher, even more preferably at 65 to 100%, and even more preferably at 80 to 98% in view of the physiologic benefits, such as a very low degree of accumulation in the human body when it is used as an edible oil. The diacylglycerol-rich fat or oil may preferably contain the monoacylglycerol at a content of 0.05 to 7%, more preferably 0.07 to 6%, even more preferably 0.08 to 4%, even more preferably 0.1 to 3%, and even more preferably 0.2 to 2% in view of the excellent appearance as an edible fat or oil, flavor as an edible oil, reduction of the smoke generated upon heating, and productivity of the fat or oil. The diacylglycerol-rich fat or oil may optionally contain a phytosterol at a content of 0.1 to 1%, more preferably 0.12 to 0.9%, and even more preferably 0.15 to 0.8% in view of favorable appearance, physiological effects, and storage stability.

The following examples further describe and demonstrate embodiments of the present invention. The examples are given only solely for the purpose of illustration and are not to be construed as limitations of the present invention.

EXAMPLES

Analysis Method (i) Composition of Glyceride

About 10 mg of the sample and 0.5 mL of trimethylsilylating agent ("silylating agent TH", manufactured by Kanto Chemical Co. Inc.) were placed in a glass sample bottle, and the bottle was hermetically sealed. The content was heated at 70° C. for 15 minutes, and to this mixture were added 1.5 mL of water and 1.5 mL of hexane. After shaking, the mixture was allowed to stand, and the upper layer was analyzed for the composition of the glyceride by gas chromatography (GLC).

(ii) Composition of Constituent Fatty Acid

About 10 mg of the sample and 0.6 mL of 0.5 mol/L solution of sodium hydroxide in methanol were placed in a glass sample bottle, and the bottle was hermetically sealed. The content was heated at 70° C. for 30 minutes, and to this mixture was added 0.6 mL of boron trifluoride-methanol reagent ("Boron trifluoride methanol complex," manufactured by Wako Pure Chemical Industries, Ltd.), and the bottle was hermetically sealed. The content was heated to 70° C. for 10 minutes, and to this mixture were added 1 mL of saturated aqueous solution of sodium chloride and 1.5 mL of hexane. After shaking, the mixture was allowed to stand, and the upper layer was dehydrated with anhydrous sodium sulfate to produce a methyl fatty acid ester. The product was analyzed by GLC.

(iii) Phytosterol

The analysis was conducted by the same procedure as the analysis of the glyceride composition (i).

Example 1

Enzymatic Esterification

[Initial Reaction]

Soybean oil was decomposed at a high pressure, a temperature of 240° C. and a reaction time of 3 hours, and subjected to wintering to obtain soybean fatty acid. The glyceride composition and the fatty acid composition of the resulting soybean fatty acid are shown in Tables 1 and 2. 1005 g of this soybean fatty acid and 157 g of glycerine (FA/GLY=2) were esterified at a temperature of 50° C., a pressure of 400 Pa, and a reaction time of 4 hours by using 50 g of immobilized lipase (Lipozyme RM IM manufactured by Novozymes), and the immobilized enzyme was separated to obtain treated oil (a).

881 g of this treated oil (a) was distilled in a wiped film evaporator (Model 2-03 manufactured by Shinko Pantec Co., Ltd. having an inner diameter of 5 cm and a heat transfer area of 0.03 m$^2$) under the operational conditions including a heater temperature of 230° C. and a pressure of 3.3 Pa to produce 613 g of oil (A) from which recycling fraction (a') had been removed by the distillation.

[First Recycling]

239 g of the recycled fraction (a'), 871 g of soybean fatty acid, and 123 g of glycerine (FA/GLY=2) were esterified at a temperature of 50° C., a pressure of 400 Pa, and a reaction time of 3 hours by using 50 g of immobilized lipase (as described above). The immobilized enzyme was separated to obtain treated oil (b).

906 g of this treated oil (b) was distilled in the wiped film evaporator (as described above) under the operational conditions of a heater temperature of 230° C. and a pressure of 3.3 Pa to produce 631 g of oil (B) from which recycling fraction (b') had been removed by the distillation.

[Second Recycling]

220 g of the recycled fraction (b'), 808 g of soybean fatty acid, and 130 g of glycerine (FA/GLY=2) were esterified by using 50 g of the immobilized lipase (as described above) at a temperature 50° C., a pressure of 400 Pa, and a reaction time of 3 hours. The Immobilized enzyme was separated to produce the treated oil (c).

909 g of this treated oil (c) was distilled in the wiped film evaporator (as described above) under the operational conditions of a heater temperature of 230° C. and a pressure of 3.3 Pa to produce 639 g of oil (C) having a particular fraction removed by the distillation.

The composition of the material used for the distillation in each step, and the composition after the distillation are shown in Table 3.

Comparative Example 1

The procedure of Example 1 was repeated by recycling a particular fraction to thereby obtain treated oil (d) (corresponding to the treated oil (c) in the procedure of Example 1).

946 g of this treated oil (d) was distilled in the wiped film evaporator (as described above) under the operational conditions of a heater temperature of 240° C., a pressure of 3.3 Pa, and a feed rate 0.8 times that of the Example 1 to produce 538 g of oil (D) having a particular fraction removed by the distillation. The results are also shown in Table 3.

TABLE 1

| Composition of soybean fatty acid (% by weight) | |
|---|---|
| Glycerine | 0.0 |
| Fatty acid | 95.7 |
| Monoacylglycerol | 1.1 |
| Diacylglycerol | 2.3 |
| Triacylglycerol | 0.2 |
| Phytosterol | 0.17 |

TABLE 2

| Composition of the fatty acids constituting the soybean fatty acid (% by weight) | | | | | | | |
|---|---|---|---|---|---|---|---|
| C14 | C16 | C16:1 | C18 | C18:1 | C18:2 | C18:3 | C20 |
| 0.1 | 2.7 | 0.1 | 0.7 | 28.1 | 60.6 | 7.3 | 0.0 |

TABLE 3

| | | Example 1 | | | Comparative Example 1 |
|---|---|---|---|---|---|
| | | Initial | 1st recycling | 2nd recycling | 2nd recycling |
| | Treated oil | a | b | c | d |
| Composition (% by weight) | Glycerine | 0.4 | 0.3 | 0.2 | 0.3 |
| | Fatty acid | 13.4 | 14.3 | 15.5 | 15.1 |
| | Monoacyl-glycerol | 16.6 | 14.2 | 14.7 | 14.4 |
| | Diacyl-glycerol | 65.0 | 64.8 | 64.2 | 65.2 |
| | Triacyl-glycerol | 3.8 | 5.5 | 4.6 | 4.1 |
| | Phytosterol | 0.21 | 0.23 | 0.23 | 0.23 |

TABLE 3-continued

|  |  | Example 1 | | | Comparative Example 1 |
| --- | --- | --- | --- | --- | --- |
|  |  | Initial | 1st recycling | 2nd recycling | 2nd recycling |
| Fat or oil after the distillation | | A | B | C | D |
| Composition (% by weight) | Glycerine | 0.0 | 0.0 | 0.0 | 0.0 |
| | Fatty acid | 0.8 | 0.7 | 0.9 | 0.5 |
| | Monoacyl-glycerol | 3.1 | 3.5 | 6.2 | 0.3 |
| | Diacyl-glycerol | 89.8 | 87.7 | 86.3 | 91.2 |
| | Triacyl-glycerol | 5.7 | 7.5 | 5.8 | 7.5 |
| | Phytosterol | 0.08 | 0.13 | 0.20 | 0.02 |

Example 2

Chemical Glycerolysis

[Initial Reaction]

Undeodorized soybean oil was used as a starting material. The glyceride composition and the constituent fatty acid composition of the soybean oil used are shown in Tables 4 and 5. To 500 g of this soybean oil and 79 g of glycerine (FA/GLY=1.2) was added 0.058 g of calcium hydroxide as a catalyst, and glycerolysis was allowed to proceed at a temperature of 235° C., normal pressure, and a reaction time of 1 hour. The mixture was cooled to a temperature of 100° C. or less, and 0.069 g of phosphoric acid was added to neutralize the catalyst and obtain treated oil (e).

565 g of this treated oil (e) was distilled in a wiped film evaporator (Model 2-03 manufactured by Shinko Pantec Co., Ltd. having an inner diameter of 5 cm and a heat transfer area of 0.03 m$^2$) under the operational conditions including a heater temperature of 230° C. and a pressure of 3.3 Pa to produce 314 g of oil (E) from which recycling fraction (e') had been removed by the distillation.

[First Recycling]

To 206 g of the recycled fraction (e'), 342 g of soybean fatty acid, and 32 g of glycerine (FA/GLY=1.2) was added 0.058 of calcium hydroxide as a catalyst, and glycerolysis was allowed to proceed at a temperature of 235° C., normal pressure, and a reaction time of 1 hour. The mixture was cooled to a temperature of 100° C. or less, and 0.069 g of phosphoric acid was added to neutralize the catalyst and obtain treated oil (f).

568 g of this treated oil (f) was distilled in the wiped film evaporator (as described above) under the operational conditions including a heater temperature of 230° C. and a pressure of 3.3 Pa to produce 311 g of oil (F) from which recycling fraction (f') had been removed by the distillation.

[Second Recycling]

To 220 g of the recycled fraction (f'), 329 g of soybean oil, and 30 g of glycerine (FA/GLY=2) were added 0.058 g of calcium hydroxide as a catalyst, and glycerolysis was allowed to proceed at a temperature of 235° C., normal pressure, and a reaction time of 1 hour. The mixture was cooled to a temperature of 100° C. or less, and 0.069 g of phosphoric acid was added to neutralize the catalyst and obtain treated oil (g).

569 g of this treated oil (g) was distilled in the wiped film evaporator (as described above) under the operational conditions including a heater temperature of 230° C. and a pressure of 3.3 Pa to produce 297 g of oil (G) having a particular fraction removed by the distillation.

Composition of the material used for the distillation in each step and the composition after the distillation are shown in Table 6.

Comparative Example 2

The procedure of Example 2 was repeated by recycling a particular fraction to thereby obtain treated oil (h) (corresponding to the treated oil (g) in the procedure of Example 2).

454 g of this treated oil (h) was distilled in the wiped film evaporator (as described above) under the operational conditions of a heater temperature of 230° C., a pressure of 1.3 Pa to produce 212 g of oil (H) having a particular fraction removed by the distillation. The results are also shown in Table 6.

TABLE 4

| Composition of soybean fatty acid (% by weight) | |
| --- | --- |
| Glycerine | 0.0 |
| Fatty acid | 0.1 |
| Monoacylglycerol | 0.0 |
| Diacylglycerol | 1.3 |
| Triacylglycerol | 98.0 |
| Phytosterol | 0.32 |

TABLE 5

| Composition of the fatty acids constituting the soybean fatty acid (% by weight) | | | | | | | |
| --- | --- | --- | --- | --- | --- | --- | --- |
| C14 | C16 | C16:1 | C18 | C18:1 | C18:2 | C18:3 | C20 |
| 0.1 | 10.4 | 0.1 | 4.5 | 24.6 | 51.7 | 7.1 | 0.4 |

TABLE 6

|  |  | Example 2 | | | Comparative Example 2 |
| --- | --- | --- | --- | --- | --- |
|  |  | Initial | 1st recycling | 2nd recycling | 2nd recycling |
| Treated oil | | e | f | g | h |
| Composition (% by weight) | Glycerine | 3.7 | 4.1 | 4.2 | 4.0 |
| | Fatty acid | 0.1 | 0.2 | 0.2 | 0.2 |
| | Monoacyl-glycerol | 42.0 | 42.9 | 43.1 | 42.6 |

TABLE 6-continued

|  |  | Example 2 | | | Comparative Example 2 |
|---|---|---|---|---|---|
|  |  | Initial | 1st recycling | 2nd recycling | 2nd recycling |
|  | Diacyl-glycerol | 39.2 | 38.9 | 38.5 | 38.8 |
|  | Triacyl-glycerol | 14.1 | 12.8 | 13.0 | 13.4 |
|  | Phytosterol | 0.35 | 0.39 | 0.40 | 0.40 |
| Fat or oil after the distillation | | E | F | G | H |
| Composition (% by weight) | Glycerine | 0.0 | 0.1 | 0.1 | 0.0 |
|  | Fatty acid | 0.0 | 0.0 | 0.0 | 0.0 |
|  | Monoacyl-glycerol | 7.9 | 5.2 | 5.1 | 0.47 |
|  | Diacyl-glycerol | 66.4 | 69.9 | 68.4 | 74.1 |
|  | Triacyl-glycerol | 25.0 | 24.1 | 25.6 | 24.9 |
|  | Phytosterol | 0.16 | 0.18 | 0.20 | 0.02 |

Example 3

Chemical Esterification

[Initial Reaction]

To 400 g of soybean fatty acid as shown in Tables 1 and 2 and 101 g of glycerine (FA/GLY=2) was added 0.050 g of calcium hydroxide as a catalyst, and esterification was allowed to proceed at a temperature of 235° C., normal pressure, and a reaction time of 1.5 hours. The mixture was cooled to a temperature of 100° C. or less, and 0.059 g of phosphoric acid was added to neutralize the catalyst and obtain treated oil (i).

452 g of this treated oil (i) was distilled in a wiped film evaporator (Model 2-03 manufactured by Shinko Pantec Co., Ltd. having an inner diameter of 5 cm and a heat transfer area of 0.03 m²) under the operational conditions including a heater temperature of 230° C. and a pressure of 3.3 Pa to produce 278 g of oil (I) from which recycling fraction (i') had been removed by the distillation.

[First Recycling]

To 146 g of the recycled fraction (i'), 286 g of soybean fatty acid, and 63 g of glycerine (FA/GLY=2) was added 0.050 of calcium hydroxide as a catalyst, and esterification was allowed to proceed at a temperature of 235° C., normal pressure, and a reaction time of 1.5 hours. The mixture was cooled to a temperature of 100° C. or less, and 0.059 g of phosphoric acid was added to neutralize the catalyst and obtain treated oil (j).

463 g of this treated oil (j) was distilled in the wiped film evaporator (as described above) under the operational conditions including a heater temperature of 230° C. and a pressure of 3.3 Pa to produce 246 g of oil (J) from which recycling fraction (j') had been removed by the distillation.

[Second Recycling]

To 185 g of the recycled fraction (j'), 259 g of soybean fatty acid, and 49 g of glycerine (FA/GLY=2) were added 0.050 g of calcium hydroxide as a catalyst, and esterification was allowed to proceed at a temperature of 235° C., normal pressure, and a reaction time of 1.5 hour. The mixture was cooled to a temperature of 100° C. or less, and 0.059 g of phosphoric acid was added to neutralize the catalyst and obtain treated oil (k).

464 g of this treated oil (k) was distilled in the wiped film evaporator (as described above) under the operational conditions including a heater temperature of 230° C. and a pressure of 3.3 Pa to produce 249 g of oil (K) having a particular fraction removed by the distillation.

Composition of the material used for the distillation in each step and the composition after the distillation are shown in Table 7.

Comparative Example 3

The procedure of Example 3 was repeated by recycling a particular fraction to thereby obtain treated oil (1) (corresponding to the treated oil (k) in the procedure of Example 3).

448 g of this treated oil (1) was distilled in the wiped film evaporator (as described above) under the operational conditions of a heater temperature of 230° C., a pressure of 1.3 Pa to produce 271 g of oil (L) having a particular fraction removed by the distillation. The results are also shown in Table 7.

TABLE 7

|  |  | Example 3 | | | Comparative Example 3 |
|---|---|---|---|---|---|
|  |  | Initial | 1st recycling | 2nd recycling | 2nd recycling |
| Treated oil | | i | j | k | l |
| Composition (% by weight) | Glycerine | 1.8 | 2.9 | 2.8 | 1.7 |
|  | Fatty acid | 0.2 | 0.5 | 0.4 | 0.3 |
|  | Monoacyl-glycerol | 35.6 | 42.5 | 41.8 | 33.8 |
|  | Diacyl-glycerol | 43.2 | 39.4 | 40.1 | 43.3 |
|  | Triacyl-glycerol | 18.4 | 13.7 | 14.1 | 20.1 |
|  | Phytosterol | 0.16 | 0.19 | 0.20 | 0.15 |
| Fat or oil after the distillation | | I | J | K | L |
| Composition (% by weight) | Glycerine | 0.0 | 0.1 | 0.0 | 0.0 |
|  | Fatty acid | 0.0 | 0.0 | 0.0 | 0.0 |

TABLE 7-continued

|  | Example 3 | | | Comparative Example 3 |
|---|---|---|---|---|
|  | Initial | 1st recycling | 2nd recycling | 2nd recycling |
| Monoacyl-glycerol | 0.9 | 1.6 | 3.8 | 0.4 |
| Diacyl-glycerol | 72.6 | 75.0 | 73.2 | 70.8 |
| Triacyl-glycerol | 25.8 | 22.7 | 22.2 | 28.1 |
| Phytosterol | 0.03 | 0.05 | 0.09 | 0.01 |

Example 4

Enzymatic Glycerolysis

[Initial Reaction]

510 g of soybean oil shown in Tables 4 and 5, 80 g of glycerine (FA/GLY=1.2) and 18 g of water were glycerolyzed by using 30 g of immobilized enzyme (Lipase AY, manufactured by Amano Enzyme Inc., immobilized on an ion exchange resin) as a catalyst at a temperature of 40° C., normal pressure, and a reaction time of 24 hours, and the immobilized enzyme was separated to obtain treated oil (m).

462 g of this treated oil (m) was distilled in a wiped film evaporator (Model 2-03 manufactured by Shinko Pantec Co., Ltd. having an inner diameter of 5 cm and a heat transfer area of 0.03 m$^2$) under the operational conditions including a heater temperature of 230° C. and a pressure of 3.3 Pa to produce 243 g of oil (M) from which recycling fraction (m') had been removed by the distillation.

[First Recycling]

176 g of the recycled fraction m', 344 g of soybean oil, 77 g of glycerine (FA/GLY=1.2) and 18 g of water were glycerolyzed by using 30 g of immobilized enzyme (Lipase AY, manufactured by Amano Enzyme Inc., immobilized on an ion exchange resin) as a catalyst at a temperature of 40° C., normal pressure, and a reaction time of 24 hours, and the immobilized enzyme was separated to obtain treated oil (n).

481 g of this treated oil (n) was distilled in the wiped film evaporator (as described above) under the operational conditions including a heater temperature of 230° C. and a pressure of 3.3 Pa to produce 218 g of oil (N) from which recycling fraction (n') had been removed by the distillation.

[Second Recycling]

176 g of the recycled fraction n', 342 g of soybean oil, 80 g of glycerine (FA/GLY=1.2) and 18 g of water were glycerolyzed by using 30 g of immobilized enzyme (Lipase AY, manufactured by Amano Enzyme Inc., immobilized on an ion exchange resin) as a catalyst at a temperature of 40° C., normal pressure, and a reaction time of 24 hours, and the immobilized enzyme was separated to obtain treated oil (o).

468 g of this treated oil (o) was distilled in the wiped film evaporator (as described above) under the operational conditions including a heater temperature of 230° C. and a pressure of 3.3 Pa to produce 249 g of oil (O) having a particular fraction removed by the distillation.

Composition of the material used for the distillation in each step and the composition after the distillation are shown in Table 8.

Comparative Example 4

The procedure of Example 4 was repeated for recycling of particular fraction to produce treated oil (p) (corresponding to the treated oil (o) in the procedure of Example 4).

480 g of this treated oil (p) was distilled in the wiped film evaporator (as described above) under the operational conditions of a heater temperature of 230° C., a pressure of 1.3 Pa to produce 209 g of oil (P) having a particular fraction removed by the distillation. The results are also shown in Table 8.

TABLE 8

|  |  | Example 4 | | | Comparative Example 4 |
|---|---|---|---|---|---|
|  |  | Initial | 1st recycling | 2nd recycling | 2nd recycling |
|  | Treated oil | m | n | o | p |
| Composition (% by weight) | Glycerine | 0.9 | 1.6 | 1.1 | 0.8 |
|  | Fatty acid | 23.8 | 29.2 | 29.6 | 24.3 |
|  | Monoacyl-glycerol | 16.3 | 15.2 | 15.6 | 16.1 |
|  | Diacyl-glycerol | 36.2 | 33.7 | 32.4 | 36.2 |
|  | Triacyl-glycerol | 21.6 | 19.2 | 20.3 | 21.6 |
|  | Phytosterol | 0.27 | 0.24 | 0.23 | 0.25 |
|  | Fat or oil after the distillation | M | N | O | P |
| Composition (% by weight) | Glycerine | 0.1 | 0.0 | 0.0 | 0.0 |
|  | Fatty acid | 0.8 | 0.4 | 3.8 | 0.3 |
|  | Monoacyl-glycerol | 0.8 | 1.6 | 5.5 | 0.1 |
|  | Diacyl-glycerol | 60.1 | 62.0 | 56.7 | 58.4 |
|  | Triacyl-glycerol | 37.3 | 35.1 | 33.0 | 40.3 |
|  | Phytosterol | 0.04 | 0.12 | 0.18 | 0.01 |

In all of the esterification of the fatty acid and the glycerine by the enzymatic and chemical methods and the glycerolysis of the oil and the glycerine by the enzymatic and chemical methods, the content of the phytosterol in the oil after the distillation was found to increase when the distillation was conducted by recycling the fraction obtained in the distillation conducted under the conditions producing an oil having a monoacylglycerol content of 0.5 to 15% compared to the oil obtained by using the fresh treated oil (initial reaction). In contrast, when the distillation was conducted by recycling the fraction obtained in the distillation conducted under the conditions producing an oil having a monoacylglycerol content of less than 0.5%, the content of the phytosterol in the oil after the distillation was low, and in such a case, the phytosterol content did not increase by the recycling.

The invention claimed is:

1. A method for producing a diacylglycerol-rich fat or oil, the method comprising:
   reacting an acyl group donor with an acyl group receptor to produce a treated fat or oil;
   separating unreacted material and byproducts from the treated fat or oil by distillation for use as a part of a starting material in a subsequent cycle of production;
   recycling the separated unreacted material and byproducts as a part of the starting material in the subsequent cycle of production,
   separating from a treated fat or oil of the subsequent cycle of production unreacted material and byproducts by distillation, and
   repeating for two or more times, the recycling of the separated unreacted material and byproducts from the treated fat or oil of the subsequent cycle of production
   wherein the distillation is conducted (i) such that a content of monoacylglycerol in the fat or oil after a distillation is 0.5 to 15% by weight, and (ii) under a pressure of 2 to 300 Pa,
   a content of diacylglycerol is at least 40% by weight, and
   a content of phytosterol is 0.1 to 1.0% by weight.

2. The method for producing a diacylglycerol-rich fat or oil according to claim 1, wherein the monoacylglycerol content in the fat or oil after the distillation is 0.5 to 10% by weight.

3. The method for producing a diacylglycerol-rich fat or oil according to claim 1 or 2, wherein the monoacylglycerol content in the treated fat or oil after the reaction is 2 to 60, and the monoacylglycerol content in the fat or oil after the distillation is 0.03 to 0.8 in relation to the monoacylglycerol in the treated fat or oil after the reaction.

4. The method for producing a diacylglycerol-rich fat or oil according to claim 1, wherein the acyl group donor is one or more selected from the group consisting of a triacylglycerol, a fatty acid, and a lower alcohol ester of a fatty acid, and the acyl group receptor is glycerol.

5. The method for producing a diacylglycerol-rich fat or oil according to claim 1, wherein the distillation is conducted under a temperature of 180 to 280° C. and a residence time of 0.2 to 30 minutes.

6. The method for producing a diacylglycerol-rich fat or oil according to claim 1, wherein the distillation is conducted in a thin film evaporator.

7. The method for producing a diacylglycerol-rich fat or oil according to claim 1 or 2, wherein the distillation is conducted under the conditions of a pressure of 2 to 100 Pa, a temperature of 180 to 280° C., and a residence time of 0.2 to 30 minutes.

8. The method for producing a diacylglycerol-rich fat or oil according to claim 1, wherein the distillation is conducted under the conditions of the pressure of 2 to 100 Pa, a temperature of 180 to 280° C., and a residence time of 0.2 to 30 minutes.

9. The method for producing a diacylglycerol-rich fat or oil according to claim 1, wherein the distillation is conducted under the pressure of 3 to 100 Pa.

* * * * *